(12) United States Patent
Gelbin et al.

(10) Patent No.: US 7,888,414 B2
(45) Date of Patent: Feb. 15, 2011

(54) LIQUID PHOSPHITE BLENDS AS STABILIZERS

(75) Inventors: Michael E. Gelbin, Middlebury, CT (US); Maurice Power, Manchester (GB); Jonathan S. Hill, Manchester (GB)

(73) Assignee: Chemtura Corporation, Middlebury, CT (US)

( * ) Notice: Subject to any disclaimer, the term of this patent is extended or adjusted under 35 U.S.C. 154(b) by 932 days.

(21) Appl. No.: 11/787,531

(22) Filed: Apr. 16, 2007

(65) Prior Publication Data

US 2010/0048782 A1    Feb. 25, 2010

Related U.S. Application Data

(60) Provisional application No. 60/815,819, filed on Jun. 20, 2006.

(51) Int. Cl.
*C08K 5/52* (2006.01)
(52) U.S. Cl. ............................................ 524/128
(58) Field of Classification Search .................. 524/128
See application file for complete search history.

(56) References Cited

U.S. PATENT DOCUMENTS

| | | | |
|---|---|---|---|
| 2,220,845 A | 11/1940 | Moyle | |
| 2,834,798 A | 5/1958 | Hechenbleikner et al. | |
| 3,056,823 A | 10/1962 | Adams et al. | 260/461 |
| 3,412,064 A | 11/1968 | Brindell | |
| 3,492,377 A | 1/1970 | Kline | |
| 3,558,554 A | 1/1971 | Kuriyama et al. | |
| 3,644,536 A | 2/1972 | Bafford | |
| 3,755,200 A | 8/1973 | Rhodes et al. | |
| 3,756,906 A | 9/1973 | Nicholas et al. | |
| 3,787,537 A | 1/1974 | De Marcq | |
| 3,948,801 A | 4/1976 | Braddon et al. | 252/400.24 |
| 4,261,880 A | 4/1981 | Fujii et al. | |
| 4,276,233 A | 6/1981 | Markezich et al. | |
| 4,321,218 A | 3/1982 | Rasberger | |
| 4,383,950 A | 5/1983 | Rasberger | |
| 4,406,842 A | 9/1983 | Spivack | |
| 4,492,661 A | 1/1985 | Maul et al. | |
| 4,829,112 A | 5/1989 | Ishii et al. | |
| 5,208,368 A | 5/1993 | Scherzer et al. | |
| 5,254,610 A | 10/1993 | Small, Jr. et al. | |
| 5,254,709 A | 10/1993 | Hunter | |
| 5,322,871 A | 6/1994 | Pitteloud et al. | |
| 5,401,845 A | 3/1995 | Pitteloud et al. | |
| 5,532,401 A | 7/1996 | Stevenson et al. | |
| 5,561,181 A | 10/1996 | Mahood | |
| 6,576,788 B1 | 6/2003 | Penzel et al. | |
| 6,824,711 B2 | 11/2004 | Stevenson et al. | 252/400.24 |
| 6,846,859 B2 | 1/2005 | Coffy et al. | |
| 6,887,926 B1 | 5/2005 | Parhar et al. | |
| 7,157,511 B2 | 1/2007 | Bobsein et al. | |
| 7,176,252 B2 | 2/2007 | Stevenson et al. | |
| 7,320,764 B2 | 1/2008 | Stevenson et al. | |
| 7,361,703 B2 | 4/2008 | Tikuisis et al. | |
| 7,468,410 B2 | 12/2008 | Chafin et al. | |
| 2003/0001136 A1 | 1/2003 | Stevenson et al. | 252/299.1 |
| 2003/0078340 A1 | 4/2003 | Fatnes et al. | |
| 2004/0048958 A1 | 3/2004 | Didier | |
| 2004/0183054 A1 | 9/2004 | Stevenson et al. | 252/400.24 |
| 2007/0149660 A1 | 6/2007 | Kumar et al. | |
| 2007/0228343 A1 | 10/2007 | Roth et al. | |

FOREIGN PATENT DOCUMENTS

| | | |
|---|---|---|
| CA | 2464551 | 11/2005 |
| CZ | 280072 | 1/1993 |
| DE | 2940620 | 4/1981 |
| DE | 4001397 | 7/1990 |
| EP | 0 090 524 | 10/1983 |
| EP | 0090524 A1 | 10/1983 |
| EP | 0 245 852 | 11/1987 |
| EP | 0245852 A2 | 11/1987 |
| EP | 0551 062 | 7/1993 |
| GB | 1 298 248 | 11/1972 |
| GB | 2 227 490 | 8/1990 |
| JP | 59 30842 | 2/1984 |
| JP | 59030842 | 2/1984 |
| JP | 5202236 | 8/1993 |
| JP | 05202236 | 8/1993 |
| JP | 7 309884 | 11/1995 |
| RO | 112871 | 1/1998 |
| RU | 2 140 938 | 11/1999 |
| WO | 9303092 | 2/1993 |

(Continued)

OTHER PUBLICATIONS

International Search Report mailed Dec. 6, 2007; of PCT Application No. PCT/US2007/009690; 3 pgs.

(Continued)

*Primary Examiner*—Ling-Siu Choi
*Assistant Examiner*—Sonya Wright
(74) *Attorney, Agent, or Firm*—Joseph Suhadolnik

(57) ABSTRACT

A composition is disclosed that comprises a blend of at least two different phosphites of the structure

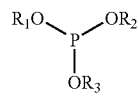

wherein $R_1$, $R_2$, and $R_3$ are independently selected alkylated aryl groups and wherein said blend is a liquid at ambient conditions. The compositions are useful for stabilizing thermoplastic resins and elastomers.

18 Claims, No Drawings

FOREIGN PATENT DOCUMENTS

| | | |
|---|---|---|
| WO | 01/62832 | 8/2001 |
| WO | 01/62833 | 8/2001 |
| WO | 02070625 | 9/2002 |
| WO | 2007009916 A1 | 1/2007 |
| WO | 2007/149143 | 12/2007 |

OTHER PUBLICATIONS

International Preliminary Report on Patentability mailed Dec. 22, 2008; of PCT Application No. PCT/US2007/009690; 6 pgs.

LIQUID PHOSPHITE BLENDS AS STABILIZERS

I claim the benefit under Title 35, United States Code, §119 to U.S. Provisional Application No. 60/815,819, filed Jun. 20, 2006 entitled LIQUID PHOSPHITE BLENDS AS STABILIZERS.

BACKGROUND OF THE INVENTION

1. Field of Invention

The present invention relates to novel mixtures of phosphite antioxidants for polymeric resin compositions. It also relates to stabilized resin compositions and stabilizer concentrates comprising said novel liquid mixtures of phosphite antioxidants.

2. Description of Related Art

Organic phosphites (aka phosphorous acid esters) are known in the art as secondary antioxidants for polyolefins, polyvinyl chloride, and elastomers. Examples of such known phosphites are given in H. Zweifel (Ed) Plastics Additives Handbook, 5$^{th}$ edition, Hanser Publishers, Munich 2000. One of the most widely used organic phosphites is trisnonylphenyl phosphite (TNPP), which is a liquid at room temperature. There is, however, a need to replace TNPP owing to the alleged estrogenicity of nonylphenol. Furthermore, as TNPP is a liquid at ambient conditions, there is a need to replace it with a phosphite that is also a liquid at ambient conditions.

Phosphite stabilizer blends, both liquid and solid, are known in the art.

U.S. Pat. No. 3,948,801 discloses stabilizing compositions comprising at least one triaryl phosphite, trialkyl phosphite or mixtures thereof and at least one modified lignin, the weight ratio of the phosphite to modified lignin being from 97/3 to 10/90. The modified lignins are produced by heat treating lignins in the presence of a nucleophile, such that a portion of the original guaiacyl structures are converted to catechols via a demethylation reaction. Elastomers are said to be protected against atmospheric degradation by the addition thereto of 0.01 to 5.0 parts by weight per 100 parts of elastomer of the stabilizing composition.

U.S. Published Patent Application No. 2003/0001136 and U.S. Pat. No. 6,824,711 disclose a liquid polymer additive composition comprising at least one phosphite ester selected from the group consisting of aryl phosphites, alkyl phosphites, aryl/alkyl phosphites, bisphenol-A phosphites, dialkylene glycol phosphites and polydialkylene glycol phosphites, pentaerythritol phosphites, p-cumyl phenol phosphites and blends thereof and approximately from 50 to 800 ppm inclusive of zinc per 100 parts resin. The stabilizer is used as either a complete or a partial replacement of toxic-metal containing antioxidant stabilizer additives.

U.S. Published Patent Application No. 2004/0183054 discloses liquid polymer additive compositions comprising blends of phosphite esters selected from the group consisting of aryl phosphites, alkyl phosphites, aryl/alkyl phosphites, bisphenol-A phosphites, dialkylene glycol phosphites and polydialkylene glycol phosphites, pentaerythritol phosphites, p-cumyl phenol phosphites with from 50 to 800 ppm inclusive of zinc per 100 parts resin. The stabilizer is used as either a complete or a partial replacement of toxic-metal containing antioxidant stabilizer additives.

U.S. Published Patent Application No. 2007/0021537 discloses a process for stabilizing polyolefin compositions against the deleterious effects of melt processing, heat aging and exposure to combustion products of natural gas, which process comprises incorporating or applying to a polyolefin an effective stabilizing amount of a tris-(mono-alkyl)phenyl phosphite ester of the formula I,

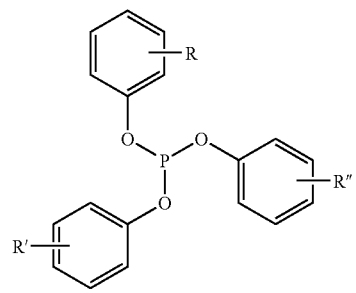

or a mixture of phosphite esters of formula I, where each R is the same or different and is straight or branched chain alkyl of from 1 to 8 carbon atoms, and where said phosphite ester or phosphite ester mixture is in the liquid state at 25° C. and 1 atm of pressure. Also disclosed is a stabilized composition comprising polyolefin and a present phosphite ester or phosphite ester mixture as well as certain mixtures of tris-(mono-alkyl)phenyl phosphite. These liquid phosphite ester stabilizers are said to be especially compatible with low density polyethylene.

CA 2,464,551 discloses solid mixtures of individually solid phosphite components for the phenol-free stabilization of polyethylene film.

CZ 280072 discloses mixtures of phosphites and phosphonites as stabilizers for propylene polymers.

DE 90-4,001,397 discloses phosphonite and phosphite esters as heat stabilizers for polymers.

JP 05202236 discloses blends comprising phosphites and phosphonites said to be useful in the production of heat-resistant polyolefin compositions.

JP 59030842 discloses solid phosphite blends comprising solid phosphites said to be useful in the stabilization of polyolefin compositions.

RO 112871 discloses compounds of the formula $(RR^1R^2C_6H_2O)_3P$ wherein (R, R$^1$, R$^2$=CMe$_2$Ph; or R=H, R$^1$, R$^2$=CMe$_2$Ph; or R=R$^1$=H, R$^2$=CMe$_2$Ph) as a mixture of triphosphites of phenol and mono-, di- and triarylalkylated phenols that consist of a mobile yellow liquid containing 4±0.3% P and 0.5% Cl and having an index of refraction of 1.5992 and d 1.1400 g/cm$^3$, said to be useful as stabilizers for polymers and elastomers (no data). The mixture is prepd. by esterification of PCl$_3$ with a mixture of phenol and mono-, di- and triarylalkylated phenols having a median molecular weight of 300 in a molar ratio of arylalkyl phenols to phenol of 1:1-1.5 and arylalkyl phenol+phenol to PCl$_3$ of 1:0.3-0.4 with no solvent or catalyst under anhydrous conditions with agitation at 25-40° for 0.5-1.5 hours, then gradually raising the temperature to 90-150°, maintaining the temperature at 150-180° or 2-6 hours, removing the HCl formed in the reaction by bubbling nitrogen through the reaction mass at 150-180° for 2-5 hours, and then removing the unreacted starting materials by distillation in an inert nitrogen atmosphere at 10 mm Hg at 175°. In the example given, 989 grams of a mixture of (1-methyl-1-phenylethyl)phenols produced by alkylation of phenol with α-methylstyrene and 475 grams of phenol are melted with stirring at 25° and 383 grams of PCl$_3$ are added dropwise over 1 hour, whereupon the mixture is gradually heated to 90°, held 1 hour at 90°, then heated to 150° and held there for 5 hours, after which the HCl formed is blown out by bubbling nitrogen through the mixture at 150° for 5 hours, after which the unreacted phenols are removed by distillation under nitrogen at 175° and 10 mm Hg pressure to give 1460 grams of a product mixture that is a yellow liquid containing 4.14% P and 0.5% Cl, with an index of refraction of 1.5992 and d 1.1400 g/cm$^3$, which contains tri-phenyl phosphite and the triphosphites of 2-(α,α-dimethylbenzyl) phenol, 4-(α,α-dimethylbenzyl)phenol, 2,6-bis(α,α-dimethylbenzyl)phenol and 2,4,6-tris(α,α-dimethylbenzyl)phenol.

WO 02070625 discloses liquid phosphite mixtures as additive compositions.

WO 2001/062832 discloses the addition of stabilizer additives to polymer particles for rotational molding.

WO 2001062833 discloses mixtures of organic phosphites and phosphonites useful in the addition of stabilizer additives for polymer particles for rotational molding.

WO 9303092 discloses the use of solid mixtures of individually solid phosphite components as heat-resistant polyester-polycarbonate molding compositions.

The disclosures of the foregoing are incorporated herein by reference in their entirety.

SUMMARY OF THE INVENTION

There is a continuing demand for liquid phosphite antioxidants in resin applications. The present invention relates to phosphite blends, preferably aryl phosphite blends, that have antioxidant properties and exist in liquid physical form at ambient conditions, i.e., atmospheric pressure and room temperature.

The individual aryl phosphite components comprising the new liquid phosphite blends are solid at room temperature. Thus, the present invention relates to the unobvious and surprising discovery that, when these solid individual aryl phosphite components comprise the phosphite blends of the present invention, the blends are in liquid physical form at ambient conditions.

The present invention further relates to a process whereby the aforementioned liquid phosphite blends can be prepared by the direct reaction of a phosphorus trihalide and a corresponding blend of alkylated phenols.

The present invention also relates to the use of these liquid phosphite blends as stabilizers/antioxidants for thermoplastic resins and elastomers.

More particularly, the present invention is directed to a composition comprising a blend of at least two different phosphites of the structure

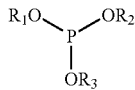

wherein $R_1$, $R_2$, and $R_3$ are independently selected alkylated aryl groups and wherein said blend is a liquid at ambient conditions.

In another aspect, the present invention is directed to a stabilized composition comprising:

(A) a polymeric resin, and (B) a stabilizing amount of a blend of at least two different phosphites of the structure

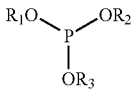

wherein $R_1$, $R_2$, and $R_3$ are independently selected alkylated aryl groups and wherein said blend is a liquid at ambient conditions.

In another aspect, the present invention is directed to an article of manufacture comprising a stabilized composition comprising:

(A) a polymeric resin, and (B) a stabilizing amount of a blend of at least two different phosphites of the structure

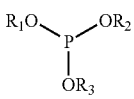

wherein $R_1$, $R_2$, and $R_3$ are independently selected alkylated aryl groups and wherein said blend is a liquid at ambient conditions.

In yet another aspect, the present invention is directed to a method for stabilizing a thermoplastic resin or elastomer comprising the step of adding to said thermoplastic resin or elastomer a stabilizing amount of a blend of at least two different phosphites of the structure

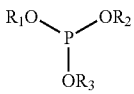

wherein $R_1$, $R_2$, and $R_3$ are independently selected alkylated aryl groups and wherein said blend is a liquid at ambient conditions.

In still another aspect, the present invention is directed to a method for synthesizing a liquid mixture of at least two liquid phosphites of the structure

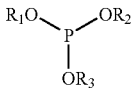

wherein $R_1$, $R_2$, and $R_3$ are independently selected alkylated aryl groups comprising reacting $PZ_3$, wherein Z is a halogen, with a mixture comprising from about 5 to about 95 weight percent of a solid p-alkylated phenol and, correspondingly, from about 95 to about 5 weight percent of a solid o,p-dialkylated phenol. Preferably, Z is chlorine or bromine, the molar ratio of the phenol mixture to the $PZ_3$ is 3:1, and the alkyl groups of the alkylated phenols are straight or branched chain alkyls of from one to six carbon atoms. More preferably, the alkyl groups of the alkylated phenols are straight or branched chain alkyls of from four to five carbon atoms; most preferably, they are tert.-butyl or tert.-pentyl.

DESCRIPTION OF THE PREFERRED EMBODIMENTS

As noted above, the present invention is directed to a composition comprising a blend of at least two different phosphites of the structure

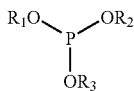

wherein $R_1$, $R_2$, and $R_3$ are independently selected alkylated aryl groups and wherein said blend is a liquid at ambient conditions.

The aryl moiety present in the compounds of the present invention is preferably an aromatic moiety of from 6 to 18 carbon atoms, e.g., phenyl, naphthyl, phenanthryl, anthracyl, biphenyl, terphenyl, and the like, preferably phenyl. Such aromatic moieties are substituted with at least one alkyl group and can be can be further substituted with any substituent(s) that will not substantially adversely affect the physical and stabilizing properties of the compounds of this invention.

The alkyl substituent or substituents of the aryl moiety are selected from the group consisting of alkyl moieties of from one to eighteen carbon atoms, e.g., methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, isomers of the foregoing, and the like. Preferably, such alkyl moieties comprise from one to six carbon atoms, which may be straight-chain or branched; more preferably four or five carbon atoms. Most preferred are butyl, especially tert-butyl, and pentyl groups, especially tert-pentyl.

In a preferred embodiment, $R_1$, $R_2$, and $R_3$ are independently selected alkylated aryl groups of the structure:

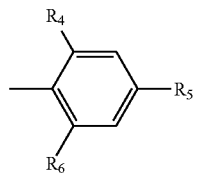

wherein $R_4$, $R_5$, and $R_6$ are independently selected from the group consisting of hydrogen and $C_1$-$C_6$ alkyl, e.g., methyl, ethyl, propyl, butyl, pentyl, hexyl, and isomers thereof, e.g., isopropyl, tert-butyl, neopentyl, and the like, provided that at least one of $R_4$, $R_5$, and $R_6$ is not hydrogen. Preferably, $R_4$, $R_5$, and $R_6$ are selected from the group consisting of hydrogen, methyl, ethyl, propyl, butyl, pentyl, and isomers thereof, again with the proviso that at least one of $R_4$, $R_5$, and $R_6$ is not hydrogen. More preferably, $R_4$, $R_5$, and/or $R_6$ are $C_4$ or $C_5$ alkyl, most preferably tert-butyl or tert-pentyl.

Thus, in a preferred embodiment, the present invention is directed to a composition comprising a blend of at least two different phosphites of the structure

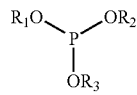

wherein $R_1$, $R_2$, and $R_3$ are independently selected alkylated aryl groups of the structure:

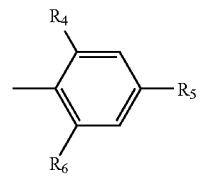

wherein $R_4$, $R_5$, and $R_6$ are independently selected from the group consisting of hydrogen and $C_1$-$C_6$ alkyl, provided that at least one of $R_4$, $R_5$, and $R_6$ is not hydrogen; and
wherein said blend is a liquid at ambient conditions.

Similarly, in another preferred embodiment, the present invention is directed to a stabilized composition comprising:
(A) a polymeric resin, and
(B) a stabilizing amount of a blend of at least two different phosphites of the structure

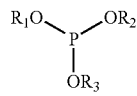

wherein $R_1$, $R_2$, and $R_3$ are independently selected alkylated aryl groups of the structure:

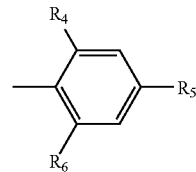

wherein $R_4$, $R_5$, and $R_6$ are independently selected from the group consisting of hydrogen and $C_1$-$C_6$ alkyl, provided that at least one of $R_4$, $R_5$, and $R_6$ is not hydrogen; and
wherein said blend is a liquid at ambient conditions.

In still another preferred embodiment the present invention is directed to an article of manufacture comprising a stabilized composition comprising:
(A) a polymeric resin, and
(B) a stabilizing amount of a blend of at least two different phosphites of the structure

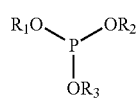

wherein $R_1$, $R_2$, and $R_3$ are independently selected alkylated aryl groups;

wherein the aryl moieties of the alkylated aryl groups present in the phosphites are independently selected from the group consisting of aromatic moieties of from 6 to 18 carbon atoms;

wherein each aryl group of the alkylated aryl groups is substituted with at least one alkyl group of from 1 to 18 carbon atoms; and wherein said blend is a liquid at ambient conditions.

In yet another preferred embodiment, the present invention is directed to a method for stabilizing a thermoplastic resin or elastomer comprising the step of adding to said thermoplastic resin or elastomer a stabilizing amount of a composition comprising a blend of at least two different phosphites of the structure

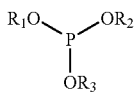

wherein $R_1$, $R_2$, and $R_3$ are independently selected alkylated aryl groups of the structure:

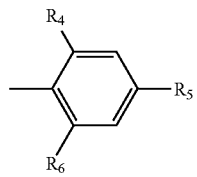

wherein $R_4$, $R_5$, and $R_6$ are independently selected from the group consisting of hydrogen and $C_1$-$C_6$ alkyl, provided that at least one of $R_4$, $R_5$, and $R_6$ is not hydrogen; and wherein said blend is a liquid at ambient conditions.

In the above-described embodiments, it is preferred that the blends comprise at least three different phosphites of the described structure, even more preferred that they comprise at least four such different phosphites.

The present invention also relates to a method whereby the liquid phosphite mixtures can be made in the direct reaction of a phosphorus trihalide and a corresponding mixture of alkyl substituted phenols, with or without catalyst. The reaction products obtained as a result of this process can be used as is, in lieu of mixing the liquid phosphite blends of the present invention, without the need for further modification. In a preferred embodiment, the present invention is directed to a method for synthesizing a liquid mixture of at least two liquid phosphites of the structure:

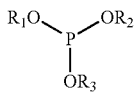

wherein $R_1$, $R_2$, and $R_3$ are independently selected alkylated aryl groups; wherein the method comprises:

(A) alkylating a phenolic compound with an alkene in the presence of an acid catalyst;

(B) separating the resulting alkylated phenol from the catalyst; and (C) reacting $PZ_3$, wherein Z is a halogen, with the resulting mixture, which comprises from about 5 to about 95 weight percent of a solid p-alkylated phenol and, correspondingly, from about 95 to about 5 weight percent of a solid o,p-dialkylated phenol. By "phenolic compound" is meant an aryl moiety, e.g., phenyl, having at least one OH group, and optionally further substituted with one or more additional groups that will not adversely affect its desirable properties, e.g., cresol, xylenol, and the like.

Thus, the preferred means for preparing the aryl phosphite stabilizers that are used in the practice of the present invention is by reacting a phosphorus trihalide, $PZ_3$, e.g., phosphorus trichloride or phosphorus tribromide, with the appropriate alkylated phenol mixture.

The reaction between the alkylated phenol mixture and the $PZ_3$ may be carried out with or without the use of a solvent. Typically, the $PZ_3$ can be added to the alkylated phenol mixture or the alkylated phenol mixture can be added to $PZ_3$. Preferably, the $PZ_3$ is added to the alkylated phenol mixture while maintaining a temperature of about 5 to 150° C. This is followed by holding the reaction mixtures for a period of 1 to 10 hours. During this period of time, HZ gas will evolve, the removal of which can be aided by either reducing the pressure or sweeping an inert gas such as nitrogen over the reaction mixture. A typical reduced pressure is 50 mbar. For HCl, for example, this step will be performed until the total Cl content is less than 50 ppm. Typically, any unreacted alkylated phenol can then be removed from the reaction mixture by further raising the temperature to up to 230° C., preferably about 200° C., while maintaining a vacuum of 5 mbar.

Desirable solvents that may be utilized are neutral solvents. Typical solvents are toluene, heptane, xylene, methylene chloride, chloroform, and benzene. Preferred solvents are methylene chloride, heptane, or xylene.

Thus, preferably, the liquid phosphite blends of the present invention are obtained in a direct chemical reaction, in which the ratio of the alkyl substituted phenols is adjusted accordingly. A schematic of the reaction method is as follows.

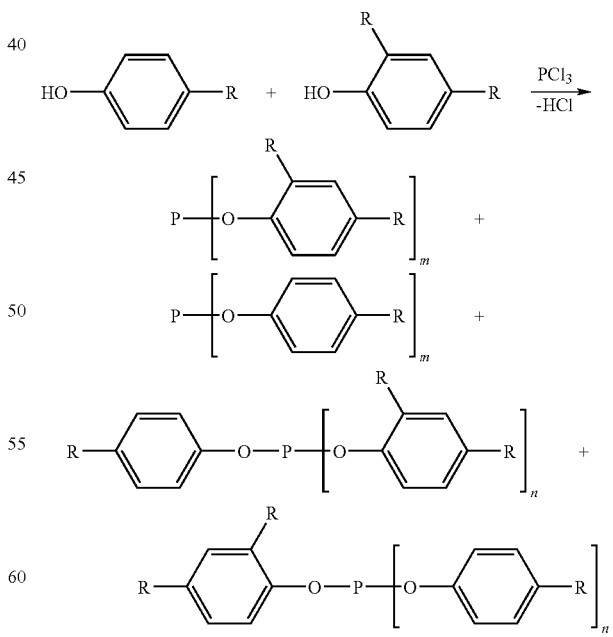

wherein m=3 and n=2.

In a preferred embodiment of the present invention, all of the above R groups are tert-butyl groups or tert.-pentyl groups and, thus, the compounds of such a blend are selected from the group consisting of tris 4-tert-butyl phenyl phosphite, tris 2,4-di-tert-butyl phenyl phosphite, bis(4-tert-butylphenyl)-2,4-di-tert-butylphenyl phosphite, bis(2,4-di-tert-butylphenyl)-4-tert-butylphenyl phosphite, tris 4-tert-pentyl phenyl phosphite, tris 2,4-di-tert-pentyl phenyl phosphite, bis(4-tert-pentylphenyl)-2,4-di-tert-pentylphenyl phosphite, and bis(2,4-di-tert-pentylphenyl)-4-tert-pentylphenyl phosphite.

As noted above, it is a feature of the present invention that the mixture of phosphite antioxidants is in liquid physical form at room temperature. This is clearly surprising, given that the prior art teaches several examples where a mixture of phosphite stabilizers, that by themselves are solids, is a solid, too, at room temperature (cf. JP 59030842; WO 9303092; CA 2,464,551). In the present invention, the blends of phosphite stabilizers form a liquid even though the individual components are known as solids.

Thus, in the schematic shown above, the liquid phosphite blend can be comprised of four main phosphite components, tris 4-tert-butyl phenyl phosphite, tris 2,4-di-tert-butyl phenyl phosphite, bis(4-tert-butylphenyl)-2,4-di-tert-butylphenyl phosphite, and bis(2,4-di-tert-butylphenyl)-4-tert-butylphenyl phosphite. However, it is known in the art, for example, that the component tris tert-butylphenyl phosphite has a melting point of 75-76° C. (Kosalopoff, Organic Phosphorus Compounds, Wiley Interscience, Vol. 5, pg 163). Likewise, tris 2,4-di-tert-butylphenyl phosphite is a solid known in the art, whose mp=181-184° C. (Aldrich catalog #441791). Similarly, bis(4-tert-butylphenyl)-2,4-di-tert-butylphenyl phosphite has a melting point of 63-65° C. Likewise, bis(2,4-di-tert-butylphenyl)-4-tert-butylphenyl phosphite has a melting point of 100-103° C.

Transesterification processes such as those disclosed in Hechenbleikner et al., U.S. Pat. No. 3,056,823, which is incorporated herein by reference, may also be employed. Specifically, the process described by Hechenbleikner et al. involves transesterifying a triaryl phosphite with a monohydroxy hydrocarbon in the presence of a small but catalytically effective amount of a metal alcoholate or metal phenolate.

To avoid contamination, the alcoholate of the particular alcohol to be transesterified is employed. Instead of employing a preformed alcoholate, the alcoholate can be formed in situ by adding the metal, e.g., sodium, potassium or lithium to the alcohol prior to adding the triaryl phosphite. The mono alcohol and triaryl phosphite are reacted in the mol ratio of three mols of the alcohol to one mol of the triaryl phosphite.

The present invention also relates to a process for making a suitable mixture of alkylated phenols. Thus, reaction of phenol (or cresol or already alkylated phenol, e.g., p-tert-butylphenol) with, preferably, a lower alkene ($C_2$-$C_6$, more preferably $C_4$-$C_5$) using any of many known catalysts (acid clays, cationic ion exchange resins, Brönsted acids e.g. sulfuric acid, Lewis acids, e.g., $BF_3$) gives a mixed alkylated phenol, the composition of which can be modified by varying the degree of alkylation, temperature, and the like.

The invention, moreover, also relates to providing a mixed alkylated phenol feedstock (for the synthesis of said phosphite blends) wherein a phenol is alkylated with a mixture of lower alkenes either in parallel (feed in alkene A and B at the same time) or consecutively (i.e. alkylate with alkene A and subsequently with alkene B).

The invention further pertains to a stabilized thermoplastic or elastomeric resin, wherein one component comprises the liquid alkyl phosphite blends and the other a polymer such as a polyolefin, polyvinyl chloride etc.

The polymer stabilized by the alkylatedaryl phosphite blends of the present invention may be any thermoplastic known in the art, such as polyolefin homopolymers and copolymers, polyesters, polyurethanes, polyalkylene terephthalates, polysulfones, polyimides, polyphenylene ethers, styrenic polymers and copolymers, polycarbonates, acrylic polymers, polyamides, polyacetals and halide-containing polymers. Mixtures of different polymers, such as polyphenylene ether/styrenic resin blends, polyvinyl chloride/ABS or other impact modified polymers, such as methacrylonitrile and alpha-methylstyrene containing ABS, and polyester/ABS or polycarbonate/ABS and polyester plus some other impact modifier may also be used. Such polymers are available commercially or may be made by means well known in the art. However, the stabilizer compositions of the invention are particularly useful in thermoplastic polymers, such as polyolefins, polycarbonates, polyesters, polyphenylene ethers and styrenic polymers, due to the extreme temperatures at which thermoplastic polymers are often processed and/or used.

Polymers of monoolefins and diolefins, for example polypropylene, polyisobutylene, polybutene-1, polymethylpentene-1, polyisoprene, or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may also be used. Also useful are copolymers of monoolefins and diolefins with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene, isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidene-norbornene; as well as mixtures of such copolymers and their mixtures with polymers mentioned above, for example polypropylene/ethylene propylene-copolymers, LDPE/EVA, LDPE/EAA, LLDPE/EVA, and LLDPE/EAA.

The olefin polymers may be produced by, for example, polymerization of olefins in the presence of Ziegler-Natta catalysts optionally on supports such as, for example, $MgCl_2$, chromium salts and complexes thereof, silica, silica-alumina and the like. The olefin polymers may also be produced utilizing chromium catalysts or single site catalysts, e.g., metallocene catalysts such as, for example, cyclopentadiene complexes of metals such as Ti and Zr. As one skilled in the art would readily appreciate, the polyethylene polymers used herein, e.g., LLDPE, can contain various comonomers such as, for example, 1-butene, 1-hexene and 1-octene comonomers.

Polymers may also include styrenic polymers, such as polystyrene, poly-(p-methylstyrene), poly-(α-methylstyrene), copolymers of styrene or α-methylstyrene with dienes or acrylic derivatives, such as, for example, styrene/butadiene, styrene/acrylonitrile, styrene/alkyl methacrylate, styrene/maleic anhydride, styrene/maleimide, styrene/butadiene/ethyl acrylate, styrene/acrylonitrile/methylacrylate, mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene styrene.

Styrenic polymers may additionally or alternatively include graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene-propylene-diene terpolymers, styrene and acrylonitrile on polyacrylates or polymethacrylates, styrene and acrylonitrile on acrylate/butadiene copolymers, as well as mixtures thereof with the styrenic copolymers indicated above.

Nitrile polymers are also useful in the polymer composition of the invention. These include homopolymers and copolymers of acrylonitrile and its analogs, such as polymethacrylonitrile, polyacrylonitrile, acrylonitrile/-butadiene polymers, acrylonitrile/alkyl acrylate polymers, acrylonitrile/alkyl methacrylate/butadiene polymers, and various ABS compositions as referred to above in regard to styrenics.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be useful. These include resins such as polychloroprene, epichlorohydrin homo- and copolymers, polyvinyl chloride, polyvinyl bromide, polyvinyl fluoride, polyvinylidene chloride, chlorinated polyethylene, chlorinated polypropylene, fluorinated polyvinylidene, brominated polyethylene, chlorinated rubber, vinyl chloride-vinyl acetate copolymers, vinyl chloride-ethylene copolymer, vinyl chloride-propylene copolymer, vinyl chloride-styrene copolymer, vinyl chloride-isobutylene copolymer, vinyl chloride-vinylidene chloride copolymer, vinyl chloride-styrene-maleic anhydride terpolymer, vinyl chloride-styrene-acrylonitrile copolymer, vinyl chloride-butadiene copolymer, vinyl chloride isoprene copolymer, vinyl chloride-chlorinated propylene copolymer, vinyl chloride-vinylidene chloride-vinyl acetate terpolymer, vinyl chloride-acrylic acid ester copolymers, vinyl chloride-maleic acid ester copolymers, vinyl chloride-methacrylic acid ester copolymers, vinyl chloride-acrylonitrile copolymer and internally plasticized polyvinyl chloride.

Other useful polymers include homopolymers and copolymers of cyclic ethers, such as polyalkylene glycols, polyethylene oxide, polypropylene oxide or copolymers thereof with bis-glycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1,4dimethylol-cyclohexane terephthalate, poly-2(2,2,4(4-hydroxyphenyl)-propane) terephthalate and polyhydroxybenzoates as well as block copolyetheresters derived from polyethers having hydroxyl end groups.

Polyamides and copolyamides which are derived from bisamides and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylene bisimine and adipic acid; polyamides prepared from hexamethylene bisimine and isophthalic or/and terephthalic acid and optionally an elastomer as modifier, for example poly-2,4,4 trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be used.

Polyolefin, polyalkylene terephthalate, polyphenylene ether and styrenic resins, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

As used herein, by "stabilizing amount" or an "effective amount" of the phosphite blends of the invention is meant when the polymer composition containing the phosphites of the invention shows improved stability in any of its physical or color properties in comparison to an analogous polymer composition which does not include a phosphite of the invention. Examples of improved stability include improved stabilization against, for example, molecular weight degradation, color degradation, and the like from, for example, melt processing, weathering, and/or long term field exposure to heat, light, and/or other elements. In one example, an improved stability is meant one or both of lower initial color or additional resistance to weathering, as measured, for example, by initial yellowness index (YI), or by resistance to yellowing and change in color, when compared to a composition without the stabilizer additive.

The invention, further, relates to a stabilized thermoplastic resin, where one component comprises the liquid aryl phosphite blends and the other a polymer such as a polyolefin, and where said liquid phosphite blend is used with a costabilizer, for example, phenolics, aromatic amines, hydroxylamines, alkylamine-N-oxides, lactones, and thioethers.

Thus, the thermoplastic resins stabilized by the phosphite blends of the present invention may optionally contain an additional stabilizer or mixture of stabilizers selected from the group consisting of the phenolic antioxidants, hindered amine stabilizers, the ultraviolet light absorbers, phosphites, phosphonites, alkaline metal salts of fatty acids, the hydrotalcites, metal oxides, epoxidized soybean oils, the hydroxylamines, the tertiary amine oxides, lactones, thermal reaction products of tertiary amine oxides, and the thiosynergists.

Thus, the resulting stabilized polymeric resin compositions optionally also contain various conventional additives, such as the following:

Antioxidants: Antioxidants may comprise alkylated monophenols, for example: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4 isobutylphenol, 2,6-dicyclopentyl-4-methylphenol, 2-(α-methylcyclohexyl)-4,6 dimethylphenol, 2,6-di-octadecyl-4-methylphenol, 2,4,6,-tricyclohexylphenol, 2,6-di-tert-butyl-4-methoxymethylphenol. Alkylated hydroquinones, for example, 2,6-di-tert-butyl-4-methoxyphenol, 2,5-di-tert-butylhydroquinone, 2,5-di-tert-amyl-hydroquinone, 2,6 diphenyl-4-octadecyloxyphenol, may also be used as antioxidants.

Antioxidants used may also comprise hydroxylated thiodiphenyl ethers, for example, 2,2'-thio-bis-(6-tert-butyl-4-methylphenol), 2,2'-thio-bis-(4-octylphenol), 4,4'-thio-bis-(6-tertbutyl-3-methylphenol), and 4,4'-thio-bis-(6-tert-butyl-2-methylphenol).

Alkylidene-bisphenols may be used as antioxidants as, for example, 2,2'-methylene-bis-(6-tert-butyl-4-methylphenol), 2,2'-methylene-bis-(6-tert-butyl-4-ethylphenol), 2,2'-methylene-bis-(4-methyl-6-(α-methylcyclohexyl)phenol), 2,2'-methylene-bis-(4-methyl-6-cyclohexylphenol), 2,2'-methylene-bis-(6-nonyl-4-methylphenol), 2,2'-methylene-bis-(6-(α-methylbenzyl)-4-nonylphenol), 2,2'-methylene-bis-(6-(α,α-dimethylbenzyl)-4-nonyl-phenol). 2,2'-methylene-bis-(4,6-di-tert-butylphenol), 2,2'-ethylidene-bis-(6-tert-butyl-4-isobutylphenol), 4,4'methylene-bis-(2,6-di-tert-butylphenol), 4,4'-methylene-bis-(6-tert-butyl-2-methylphenol), 1,1-bis-(5-tert-butyl-4-hydroxy-2-methylphenol)butane, 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy2-methylphenyl)-3-dodecyl-mercaptobutane, ethyleneglycol-bis-(3,3-bis-(3'-tert-butyl-4'-hydroxyphenyl)-butyrate)-di-(3-tert-butyl-4-hydroxy-5-methylphenyl)-dicyclopentadiene, di-(2-(3'-tert-butyl-2'-hydroxy-5'-methylbenzyl)-6-tert-butyl-4-methylphenyl)terephthalate, and other phenolics, such as monoacrylate esters of bisphenols, such as ethylidene bis-2,4-di-t-butylphenol monoacrylate ester and esters of 3-5 di butyl hydroxyphenyl propionic acid. The phenolic antioxidants of particular interest are selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxybenzylphosphonate, 1,3,5-tris(3,5-di-tert-butyl-4-hydroxybenzyl)-isocyanurate, thiodiethylene bis (3,5-di-tert-butyl-4-hydroxyhydrocinnamate), 1,3,5-trimethyl-2,4,6-tris(3,5-di-tert-butyl-4-hydroxybenzyl) benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocyanurate, 1,1,3-tris(2-methyl-4-hydroxy-5-tert-butylphenyl)butane, 1,3,5-tris[2-(3,5-di-tert-butyl-4-hydroxyhydrocinnamoyloxy) ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis-[2-(3,5-di-tert-butyl-4-hydroxyhydrocinnamoyloxy)ethyl]-oxamide.

Other antioxidants that may be used include benzyl compounds, for example, 1,3,5-tris-(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hydroxybenzyl-mercaptoacetate, bis-(4-tert-butyl-3-hydroxy-2,6-dimethylbenzyl)dithiol-terephthalate, 1,3,5-tris-(3,5-di-tert-butyl-4,10 hydroxybenzyl)isocyanurate, 1,3,5-tris-(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tertbutyl-4-hydroxybenzylphosphonate, and 1,3,5-tris-(3,5-dicyclohexyl-4-hydroxybenzyl)isocyanurate.

Acylaminophenols may be used as antioxidants, for example, 4-hydroxy-lauric acid anilide, 4-hydroxy-stearic acid anilide, 2,4-bis-octylmercapto-6-(3,5-tert-butyl-4-hydroxyanilino)-s-triazine, and octyl-N-(3,5-di-tert-butyl-4-hydroxyphenyl)-carbamate.

Esters of β-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, and dihydroxyethyl oxalic acid diamide may also be used as antioxidants.

Antioxidants may also comprise amides of β-(3,5-di-tert-butyl-4hydroxyphenol)-propionic acid, for example, N,N'-di-(3,5-di-tert-butyl-4-hydroxyphenylpropionyl)-hexamethylendiamine, N,N'-di-(3,5-di-tert-butyl-4-hydroxyphenylpropionyl)trimethylenediamine, and N,N'-di (3,5-di-tert-butyl-4-hydroxyphenylpropionyl)-hydrazine.

UV absorbers and light stabilizers may comprise 2-(2'-hydroxyphenyl)-benzotriazoles, for example, the 5'-methyl-, 3'5'-di-tert-butyl-,5'-tert-butyl-,5'(1,1,3,3-tetramethylbutyl)-, 5-chloro-3',5'-di-tert-butyl-,5-chloro-3'-tert-butyl-5'-methyl-3'-sec-butyl-5'-tert-butyl-,4'-octoxy,3',5'-di-tert-amyl-3',5'-bis-(α,α-dimethylbenzyl)-derivatives. 2-Hydroxy-benzophenones, for example, the 4-hydroxy-4-methoxy-, 4-octoxy, 4-decyloxy-, 4dodecyloxy-,4-benzyloxy,4,2',4'-trihydroxy- and 2'-hydroxy-4,4'-dimethoxy derivatives may also be used as UV absorbers and light stabilizers. UV absorbers and light stabilizers may also comprise esters of substituted and unsubstituted benzoic acids, for example, phenyl salicylate, 4-tert-butylphenyl salicylate, octylphenyl salicylate, dibenzoylresorcinol, bis-(4-tert-butylbenzoyl)-resorcinol, benzylresorcinol, 2,4-di-tert-butyl-phenyl-3,5-di-tert-butyl-4-hydroxybenzoate, and hexadecyl-3,5-di-tert-butyl-4-hydroxybenzoate.

Acrylates, for example, α-cyano-β,β-diphenylacrylic acid-ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, and N-(β-carbomethoxy-β-cyano-vinyl)-2-methyl-indoline may be used as UV absorbers and light stabilizers.

Other examples for UV absorbers and light stabilizers include nickel compounds, for example, nickel complexes of 2,2'-thio-bis(4-(1,1,1,3-tetramethylbutyl)-phenol), such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

Sterically hindered amines may be used as UV absorbers and light stabilizers as for example bis(2,2,6,6-tetramethylpiperidyl)-sebacate, bis-5 (1,2,2,6,6-pentamethylpiperidyl)-sebacate, n-butyl-3,5-di-tert-butyl-4-hydroxybenzyl malonic acid bis(1,2,2,6,6,-pentamethylpiperidyl)ester, condensation product of 1-hydroxyethyl-2,2,6,6-tetramethyl-4-hydroxypiperidine and succinic acid, condensation product of N,N'-

(2,2,6,6-tetramethylpiperidyl)-hexamethylendiamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetra-arbonic acid, 1,1'(1,2-ethanediyl)-bis-(3,3,5,5-tetramethylpiperazinone). These amines, typically called HALS (Hindered Amine Light Stabilizers), include butane tetracarboxylic acid 2,2,6,6-tetramethyl piperidinol esters. Such amines include hydroxylamines derived from hindered amines, such as di(1-hydroxy-2,2,6,6-tetramethylpiperidin-4-yl) sebacate; 1-hydroxy-2,2,6,6-tetramethyl-4-benzoxypiperidine; 1-hydroxy-2,2,6,6-tetramethyl-4-(3,5-di-tert-butyl-4-hydroxy hydrocinnamoyloxy)-piperidine; and N-(1-hydroxy-2,2,6,6-tetramethyl-piperidin-4-yl)-epsiloncaprolactam.

UV absorbers and light stabilizers may also comprise oxalic acid diamides, for example, 4,4'-di-octyloxy-oxanilide, 2,2'-di-octyloxy-5',5'-ditert-butyloxanilide, 2,2'-didodecyloxy-5',5'di-tert-butyl-oxanilide, 2-ethoxy-2'-ethyloxanilide, N,N'-bis(3-dimethylaminopropyl)-oxalamide, 2-ethoxy-5-tert-butyl-2'-ethyloxanilide and its mixture with 2-ethoxy-2'-ethyl-5,4-di-tert-butyloxanilide and mixtures of ortho- and para-methoxy-, as well as of o- and p-ethoxy-, disubstituted oxanilides.

UV absorbers and light stabilizers also include hydroxyphenyl-s-triazines, as, for example, 2,6-bis-(2,4-dimethylphenyl)-4-(2-hydroxy-4-octyloxyphenyl)-s-triazine, 2,6-bis(2,4-dimethylphenyl)-4-(2,4-dihydroxyphenyl)-s-triazine; 5 2,4-bis(2,4-dihydroxyphenyl)-6-(4-chlorophenyl)-s-triazine; 2,4-bis(2-hydroxy-4-(2-hydroxyethoxy)phenyl)-6-(4-chlorophenyl)-s-triazine; 2,4-bis(2-hydroxy-4-(2-hydroxyethoxy)phenyl)-6-phenyl-s-triazine; 2,4-bis(2-hydroxy-4-(2-hydroxyethoxy)-phenyl)-6-(2,4-dimethylphenyl)-s-triazine; 2,4-bis(2-hydroxy-4-(2-hydroxyethoxy)phenyl)-6-(4-bromo-phenyl)-s-triazine; 2,4-bis(2-hydroxy-4-(2-acetoxyethoxy)phenyl)-6-(4-chlorophenyl)-s-triazine, 2,4-bis(2,4-dihydroxyphenyl)-6-(2,4-dimethylphenyl)-1-s-triazine.

Metal deactivators as, for example, N,N'-diphenyloxalic acid diamide, N-salicylal-N'-salicyloylhydrazine, N,N'-bissalicyloylhydrazine, N,N'-bis-(3,5-di-tert-butyl-4-hydrophenylpropionyl)-2-hydrazine, salicyloylamino-1,2,4-triazole, and bis-benzyliden-oxalic acid dihydrazide, may also be used.

Phosphites and phosphonites, as, for example, triphenyl phosphite, diphenylalkyl phosphites, phenyldialkyl phosphites, tris(nonyl-phenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, 2,4,6-tri-tert-butylphenyl-2-butyl-2-ethyl-1,3-propanediol phosphite, bis(2,4-di-tert-butylphenyl)pentaerythritol diphosphite, bis(2,4-di-cumyl)pentaerythritol diphosphite, tristearyl sorbitol triphosphite, and tetrakis(2,4-di-tert-butylphenyl)4,4'-biphenylene diphosphonate may be used in some embodiments of the invention in addition to the phosphites of the invention.

Peroxide scavengers, as, for example, esters of beta-thiodipropionic acid, for example the lauryl, stearyl, myristyl or tridecyl esters, mercaptobenzimidazole or the zinc salt of 2-mercaptobenzimidazole, zinc-dibutyldithiocarbamate, dioctadecyldisulfide, and pentaerythrotetrakis-($\beta$-dodecylmercapto)-propionate may be used.

Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecyl hydroxylamine, N-heptadecyl-N-octadecylhydroxylamine, and N,N-dialkylhydroxylamine derived from hydrogenated tallow amine may also be used in some embodiments of the present invention.

Nitrones, for example, N-benzyl-$\alpha$-phenyl nitrone, N-ethyl-$\alpha$-methyl nitrone, N-octyl-$\alpha$-heptyl nitrone, N-lauryl-$\alpha$-undecyl nitrone, N-tetradecyl-$\alpha$-tridecyl nitrone, N-hexadecyl-$\alpha$-pentadecyl nitrone, N-octadecyl-$\alpha$-heptadecylnitrone, N-hexadecyl-$\alpha$-heptadecylnitrone, N-octadecyl-$\alpha$-pentadecyl nitrone, N-heptadecyl-$\alpha$-heptadecyl nitrone, N-octadecyl-$\alpha$-hexadecyl nitrone, and nitrone derived from N,N-dialkylhydroxylamine derived from hydrogenated tallow amine may also be used.

Polyamide stabilizers, for example, copper salts in combination with iodides and/or phosphorus compounds and salts of divalent manganese.

Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, Ca stearate, calcium stearoyl lactate, calcium lactate, Zn stearate, Mg stearate, for example, Na ricinoleate and K palmitate, antimony pyrocatecholate or zinc pyrocatecholate, including neutralizers, such as hydrotalcites and synthetic hydrotalcites, and Li, Na, Mg, Ca, and Al hydroxy carbonates may be used in other embodiments of the present invention, as, also, MgZn hydroxycarbonates, MgAl hydroxycarbonates and AlZn hydroxycarbonates, and metal oxides, such as ZnO, MgO, and CaO.

Nucleating agents, for example, 4-tert-butylbenzoic acid, adipic acid, diphenylacetic acid, sodium salt of methylene bis-2,4-dibutylphenyl, cyclic phosphate esters, sorbitol trisbenzaldehyde acetal, and the sodium salt of bis(2,4-di-t-butylphenyl) phosphate or the Na salt of ethylidene bis(2,4-di-t-butyl phenyl)phosphate may also be used in some embodiments.

Fillers and reinforcing agents may comprise, for example, calcium carbonate, silicates, glass fibers, asbestos, talc, kaolin, mica, barium sulfate, metal oxides and hydroxides, carbon black and graphite.

Other additives may be, for example, plasticizers, epoxidized vegetable oils, such as epoxidized soybean oils, lubricants, emulsifiers, pigments, optical brighteners, flameproofing agents, anti-static agents, blowing agents and thiosynergists, such as dilaurylthiodipropionate or distearylthiodipropionate, and the like.

The additives and stabilizers described herein are preferably present in an amount effective to improve composition stability. When one of the aforementioned additives and stabilizers is utilized, the amount is generally less than about 5 weight percent based on the weight of the resin and is preferably at least about 50 ppm based on the weight of the resin. The stabilizer combinations of this invention stabilize resins especially during high temperature processing with relatively little change in melt index and/or color, even though the polymer may undergo a number of extrusions. The instant stabilizers may readily be incorporated into the resins by conventional techniques, at any convenient stage prior to the manufacture of shaped articles therefrom. For example, the stabilizer may be mixed with the resin in dry powder form, or a suspension or emulsion of the stabilizer may be mixed with a solution, suspension, or emulsion of the polymer. The stabilized compositions of the invention may optionally also contain from about 0.001 to about 5%, preferably from about 0.0025 to about 2%, and especially from about 0.005% to about 1%, by weight of various conventional additives, such as those described previously, or mixtures thereof.

The stabilizers of this invention advantageously assist with the stabilization of polymer resin compositions especially in high temperature processing against changes in melt index and/or color, even though the polymer resin may undergo a number of extrusions. The stabilizers of the present invention may readily be incorporated into the resin compositions by conventional techniques, at any convenient stage prior to the manufacture of shaped articles therefrom. For example, the stabilizer may be mixed with the resin in dry powder form, or a suspension or emulsion of the stabilizer may be mixed with a solution, suspension, or emulsion of the polymer.

The compositions of the present invention can be prepared by a variety of methods, such as those involving intimate admixing of the ingredients with any additional materials desired in the formulation. Suitable procedures include solution blending and melt blending. Because of the availability of melt blending equipment in commercial polymer processing facilities, melt processing procedures are generally preferred. Examples of equipment used in such melt compounding methods include: co-rotating and counter-rotating extruders, single screw extruders, disc-pack processors and various other types of extrusion equipment. In some instances, the compounded material exits the extruder through small exit holes in a die and the resulting strands of molten resin are cooled by passing the strands through a water bath. The cooled strands can be chopped into small pellets for packaging and further handling.

All of the ingredients may be added initially to the processing system, or else certain additives may be pre-compounded with each other or with a portion of the polymeric resin to make a stabilizer concentrate. Moreover, it is also sometimes advantageous to employ at least one vent port to allow venting (either atmospheric or vacuum) of the melt. Those of ordinary skill in the art will be able to adjust blending times and temperatures, as well as component addition location and sequence, without undue additional experimentation.

While the stabilizers of this invention may be conveniently incorporated by conventional techniques into polymeric resins before the fabrication thereof into shaped articles, it is also possible to apply the instant stabilizers by a topical application to the finished articles. Articles may comprise the instant stabilizer compounds and resins and may be made into, for example, head lamp covers, roofing sheets, telephone covers, aircraft interiors, building interiors, computer and business machine housings, automotive parts, and home appliances. The articles may be made by extrusion, injection molding, roto-molding, compaction, and other methods. This may be particularly useful with fiber applications where the instant stabilizers are applied topically to the fibers, for example, by way of a spin finish during the melt spinning process.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

EXAMPLES

Example 1

Synthesis of Butylated Phenolic Alkylate

Phenol (188.4 grams, 2.00 moles) and Fulcat 22B catalyst (1.41 grams) were charged to an oil jacketed flask and heated to 110° C. under nitrogen. Isobutylene (180.5 grams, 3.21 moles) was added via a sintered glass frit below the surface of the phenol at a uniform rate over 4.5 hours. After the addition was completed, the reaction mass was held at a jacket temperature of 110° C. for one hour. The reaction mass was filtered and the phenolic filtrate collected. The butylated phenolic alkylate was subjected to vacuum distillation to reduce the phenol content to less than 0.25% and the water content to less than 50 ppm. Yield=290.3 grams.

Example 2

Phosphite Synthesis from a Butylated Phenolic Alkylate Obtained as Per Example 1

Butylated phenolic alkylate (152.4 grams, 0.971 mole) was charged to an oil jacketed flask and heated to 85° C. under nitrogen. $PCl_3$ (40.4 grams, 0.294 mole) was added, below the surface of the phenolics, at a uniform rate over three hours. During the addition the temperature was ramped to 150° C. The reaction mass was held at 150° C. until HCl evolution ceased, and then heated to 200° C. over one hour while the pressure was reduced from 1000 to 50 mbar. The reaction was held at 200° C./50 mbar until the total Cl content was less than 50 ppm. The phenolic excess was removed by distillation under one mbar pressure and an internal temperature of 250° C. (vapor temperature 145° C.). Yield=115.9 grams.

Temperature vs. Viscosity Profile for the Phosphite Mixture Obtained as Per Example 2

| Temperature (° C.) | Viscosity (cSt) |
| --- | --- |
| 30 | 3662 |
| 40 | 1662 |
| 50 | 494 |

Example 3

Phosphite Synthesis from a 2:1 4-Tert-Butylphenol/2,4-Di-Tert-Butylphenol Mixture Made Up from Phenol Components 4-tert-Butylphenol (176.6 grams, 11.18 moles) and 2,4-di-tert-butylphenol (121.3 grams, 0.59 mole) were charged to an oil jacketed flask and heated to 80° C. under nitrogen. $PCl_3$ (73.4 grams, 0.53 mole) was added, below the surface of the phenolics, at a uniform rate over two hours. During the addition, the temperature was ramped to 150° C. The reaction mass was held at 150° C. until HCl evolution ceased, and then was heated to 200° C. over one hour while the pressure was reduced from 1000 to 70 mbar. The reaction was held at 200° C./70 mbar until the total Cl content was less than 50 ppm.

The phenolic excess was then removed by distillation under 8 mbar pressure and an internal temperature of 200° C. Yield=279.3 grams. This product will be referred to hereinafter as Liquid Phosphite P-2.

Temperature Vs. Viscosity Profile for the Phosphite Mixture Obtained as Per Example 3

| Temperature (° C.) | Viscosity (cSt) |
|---|---|
| 40 | 8300 |
| 50 | 1776 |
| 60 | 530 |
| 70 | 218 |
| 80 | 120 |

Example 4

Synthesis of Mixed Amyl/Butyl Phenols

Phenol (105 grams, 1.12 moles) and Fulcat 22B catalyst (2.25 grams) were charged to an oil jacketed flask and heated to 130° C. under nitrogen. Isobutylene (64.6 grams, 1.15 moles) was added via a sintered glass frit below the surface of the phenol at a uniform rate over 30 minutes. During addition, the internal temperature rose to 140° C. Once the addition was completed, the reaction mass was held at a jacket temperature of 130° C. for one hour. Amylene (39.2 grams, 0.56 mole) was then added below the surface of the phenolics at a uniform rate over 1.25 hours. After the addition, the reaction mass was held at a jacket temperature of 130° C. for two hours. The reaction was then filtered and the phenolic filtrate collected. The mixed butylated/amylated phenol alkylate was subjected to vacuum distillation to reduce the phenol content to less than 0.25% and the water content to less than 50 ppm. Yield=161.8 grams.

Example 5

Conversion to a Phosphite of the Alkylate Obtained as Per Example 4

Mixed butylated/amylated phenolic alkylate (148.7 grams, 0.86 mole) was charged to an oil jacketed flask and heated to 80° C. under nitrogen. $PCl_3$ (35.8 grams, 0.26 mole) was added, below the surface of the phenolics, at a uniform rate over three hours. During the addition, the temperature was ramped to 150° C. The reaction mass was held at 150° C. until HCl evolution ceased, and then was heated to 200° C. over one hour while the pressure was reduced from 1000 to 50 mbar. The reaction was held at 200° C./50 mbar until the total Cl content was less than 50 ppm. The phenolic excess was then removed by distillation under one mbar pressure and an internal temperature of 240° C. (vapor temperature 140° C.). Yield=123.1 grams.

Temperature Vs. Viscosity Profile for the Phosphite Mixture Obtained as Per Example 5

| Temperature (° C.) | Viscosity (cSt) |
|---|---|
| 30 | 7481 |
| 40 | 3198 |
| 50 | 763 |

Example 6

Synthesis of Amyl Alkylate

Phenol (150 grams, 1.59 moles) and Fulcat 22B catalyst (3.36 grams) were charged to an oil jacketed flask and heated to 130° C. under nitrogen. Amylene (167.7 grams, 2.39 moles) was then added below the surface of the phenolics at a uniform rate over four hours. After the addition, the reaction mass was held at a jacket temperature of 130° C. for two hours. The reaction was then filtered and the phenolic filtrate collected. The amylated phenolic alkylate was purified by distillation with the main fraction being collected between 120 to 146° C. (vapor temperature=120 to 140° C.) at 5-7 mbar pressure. Yield=227.3 grams.

Example 7

Phosphite Preparation from an Amylated Phenolic Alkylate

Amylated phenolic alkylate (214.7 grams) and N,N-dimethyldodecylamine (0.65 mL) was charged to an oil jacketed flask and heated to 80° C. under nitrogen. $PCl_3$ (51.9 grams, 0.38 mole) was added below the surface of the phenolics at a uniform rate over three hours. During the addition, the temperature was ramped to 150° C. The reaction mass was held at 150° C. until HCl evolution ceased, and then was heated to 200° C. over one hour while the pressure was reduced from 1000 to 130 mbar. The reaction was held at 200° C./130 mbar until the total Cl content was less than 50 ppm. The phenolic excess was then removed by distillation under 3 mbar pressure and an internal temperature of 195° C. Yield=223.7 grams. This product will be referred to hereinafter as Liquid Phosphite P-4.

Temperature Vs. Viscosity Profile for the Phosphite Mixture Obtained as Per Example 7

| Temperature (° C.) | Viscosity (cSt) |
|---|---|
| 40 | 1270 |
| 50 | 513 |
| 60 | 238 |
| 70 | 132 |
| 80 | 75 |

Example 8

Performance Evaluation by Multipass Extrusion in Poly(propylene)

This example illustrates the stabilizing effectiveness of the liquid phosphite mixtures of the present invention upon multipass extrusion in poly(propylene).

The base polymer was a Basell HF500N Spheripol homopolymer poly(propylene) powder with a melt-flow index (MFI) of 12 grams/10 minutes. The base formulation also contained 500 ppm of calcium stearate as an acid scavenger. All formulations were made up by adding 500 ppm each of Anox 20 (tetrakis[methylene{3,5-di-tert-butyl-4-hydroxycinnamate}]methane) and a corresponding liquid phosphite mixture of the present invention to the base polymer. The thus-stabilized resin formulation was extruded from a 19 mm diameter Brabender single-screw extruder at 60 rpm, with the four heating zones being set to the following temperatures: 200° C.; 225° C.; 250° C. and 270° C. under oxygen.

The extrudate was cooled by passing it through an ice water bath and then pelletized. These pellets were re-extruded. After the third extrusion pass the melt flow rate (in g/10 min) was measured at 230° C./2.16 kg. A relatively small increase in melt flow index means insignificant polymer degradation, or good stabilization. The results are shown in Table 1.

TABLE 1

MFI Results

| Stabilizer (ppm) | Extrusion Pass 3 MFI (g/10 min) |
|---|---|
| Base | 32.0 |
| Liquid Phosphite P-2 (500) + Anox 20 (500) | 14.7 |
| Liquid Phosphite P-3 (500) + Anox 20 (500) | 13.8 |
| Liquid Phosphite P-4 (500) + Anox 20 (500) | 14.6 |

Liquid Phosphite P-2: Obtained as shown in Example 3;
Liquid Phosphite P-3: Phosphite mixture obtained from a butylated p-cresol alkylate, synthesized as shown under Example 2 by using a butylated p-cresol alkylate instead of butylated phenolic alkylate.
Liquid Phosphite P-4: Obtained as shown in Example 7.

The results from this study showed that the liquid phosphite mixtures P-2 to P-4 of the present invention gave superior melt stabilization, when compared to a control. Thus, the formulations containing a liquid phosphite mixture gave only a relatively small increase in melt flow rate compared to a control.

Example 9

Performance Evaluation in High Density Poly(ethylene)

This example illustrates the stabilizing effectiveness of the liquid phosphite mixtures of the present invention upon Plasticorder testing.

The base formulation comprised a Solvay HP-54-60 high density poly(ethylene) polymer flake and 300 ppm of Anox 20 (tetrakis[methylene{3,5-di-tert-butyl-4-hydroxycinnamate}]methane). The test formulations were made up by adding a 1000 ppm of the corresponding liquid phosphite mixtures of the present invention to the base formulation.

For the Plasticorder test, each formulation including the Base control was added to a Brabender Plastograph fitted with a 60 cc mixing head at 220° C./60 rpm. While kneading the test formulations in the mixing head, torque was continuously measured and recorded. After an induction period, the polymer began to cross-link, which could be seen as a significant increase in torque. Table 2 presents the time in minutes for the induction period preceding the onset of torque. A relatively long induction time is indicative of superior stabilization.

TABLE 2

Plasticorder Test

| Stabilizer (ppm) | Induction Time (minutes) |
|---|---|
| (A): HDPE Flake + Anox 20 (300) | 10 |
| (B): (A) + Liquid Phosphite P-2 (1000) | 22 |
| (C): (A) + Liquid Phosphite P-3 (1000) | 28 |
| (D): (A) + Liquid Phosphite P-4 (1000) | 24 |

The results of this testing showed that liquid phosphite blends P-2 to P-4 afforded superior melt stabilization to an HDPE polymer, as compared to a control. Thus, the formulations containing P-2 to P-4 gave a relatively long induction time in the Plasticorder test, as compared to a control without the phosphite.

In view of the many changes and modifications that can be made without departing from principles underlying the invention, reference should be made to the appended claims for an understanding of the scope of the protection to be afforded the invention.

What is claimed is:

1. A composition comprising a phosphite blend, said phosphite blend consisting of at least two different phosphites of the structure

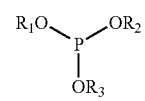

wherein $R_1$, $R_2$, and $R_3$ are independently selected alkylated aryl groups of the structure

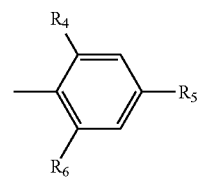

wherein $R_4$, $R_5$, and $R_6$ are independently selected from the group consisting of hydrogen and $C_1$-$C_6$ alkyl, and at least one of $R_4$, $R_5$, and $R_6$ in each phosphite is selected from the group consisting of tert-butyl and tert-pentyl, which blend of phosphites is prepared by reacting a phosphorous trihalide with a mixture of phenols said mixture of phenols comprising a p-alkylated phenol and an o,p-dialkylated phenol and wherein said phosphite blend is a liquid at room temperature and atmospheric pressure.

2. The composition of claim 1 wherein said composition comprises a blend of at least three different phosphites of the structure

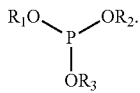

3. The composition of claim 1 wherein said composition comprises a blend of at least four different phosphites of the structure

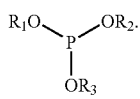

4. The composition of claim 1 wherein $R_4$, $R_5$, and $R_6$ in each phosphite is selected from the group consisting of hydrogen, tert-butyl and tert-pentyl.

5. The composition of claim 2 wherein $R_4$, $R_5$, and $R_6$ in each phosphite is selected from the group consisting of hydrogen, tert-butyl and tert-pentyl.

6. The composition of claim 3 wherein $R_4$, $R_5$, and $R_6$ in each phosphite is selected from the group consisting of hydrogen, tert-butyl and tert-pentyl.

7. The composition of claim 1 wherein the phosphites either are independently selected from the group consisting of tris 4-tert-butyl phenyl phosphite, tris 2,4-di-tert-butyl phenyl phosphite, bis(4-tert-butylphenyl)-2,4-di-tert-butylphenyl phosphite, and bis(2,4-di-tert-butylphenyl)-4-tert-butylphenyl phosphite, or are independently selected from the group consisting of tris 4-tert-pentyl phenyl phosphite, tris 2,4-di-tert-pentyl phenyl phosphite, bis(4-tert-pentylphenyl)-2,4-di-tert-pentylphenyl phosphite, and bis(2,4-di-tert-pentylphenyl)-4-tert-pentylphenyl phosphite.

8. The composition of claim 7 wherein said composition comprises a blend of at least three different phosphites either independently selected from the group consisting of tris 4-tert-butyl phenyl phosphite, tris 2,4-di-tert-butyl phenyl phosphite, bis(4-tert-butylphenyl)-2,4-di-tert-butylphenyl phosphite, and bis(2,4-di-tert-butylphenyl)-4-tert-butylphenyl phosphite, or independently selected from the group consisting of tris 4-tert-pentyl phenyl phosphite, tris 2,4-di-tert-pentyl phenyl phosphite, bis(4-tert-pentylphenyl)-2,4-di-tert-pentylphenyl phosphite, and bis(2,4-di-tert-pentylphenyl)-4-tert-pentylphenyl phosphite.

9. The composition of claim 7 wherein said composition comprises a blend of at least four different phosphites either independently selected from the group consisting of tris 4-tert-butyl phenyl phosphite, tris 2,4-di-tert-butyl phenyl phosphite, bis(4-tert-butylphenyl)-2,4-di-tert-butylphenyl phosphite, and bis(2,4-di-tert-butylphenyl)-4-tert-butylphenyl phosphite, or independently selected from the group consisting of tris 4-tert-pentyl phenyl phosphite, tris 2,4-di-tert-pentyl phenyl phosphite, bis(4-tert-pentylphenyl)-2,4di-tert-pentylphenyl phosphite, and bis(2,4-di-tert-pentylphenyl)-4-tert-pentylphenyl phosphite.

10. The composition according to claim 1 further comprising a polymer resin.

11. The composition according to claim 2 further comprising a polymer resin.

12. The composition according to claim 3 further comprising a polymer resin.

13. The composition according to claim 4 further comprising a polymer resin.

14. The composition according to claim 5 further comprising a polymer resin.

15. The composition according to claim 6 further comprising a polymer resin.

16. The composition according to claim 7 further comprising a polymer resin.

17. The composition according to claim 8 further comprising a polymer resin.

18. The composition according to claim 9 further comprising a polymer resin.

* * * * *